(12) United States Patent
Yang et al.

(10) Patent No.: US 9,783,629 B2
(45) Date of Patent: Oct. 10, 2017

(54) LOOP-ROUTE PRODUCTION METHOD AND SYSTEM FOR POLYVINYL CHLORIDE

(71) Applicant: Beijing University of Chemical Technology, Beijing (CN)

(72) Inventors: Weimin Yang, Beijing (CN); Hua Yan, Beijing (CN); Dongsheng Liu, Beijing (CN); Jinguang Zhong, Xiamen (CN)

(73) Assignee: Beijing University of Chemical Technology, Beijing (CN)

( * ) Notice: Subject to any disclaimer, the term of this patent is extended or adjusted under 35 U.S.C. 154(b) by 113 days.

(21) Appl. No.: 14/904,499

(22) PCT Filed: Dec. 19, 2013

(86) PCT No.: PCT/CN2013/089907
§ 371 (c)(1),
(2) Date: Jan. 12, 2016

(87) PCT Pub. No.: WO2015/007059
PCT Pub. Date: Jan. 22, 2015

(65) Prior Publication Data
US 2016/0168297 A1 Jun. 16, 2016

(30) Foreign Application Priority Data
Jul. 17, 2013 (CN) .......................... 2013 1 0300933

(51) Int. Cl.
*C08F 2/00* (2006.01)
*C08F 14/06* (2006.01)
(Continued)

(52) U.S. Cl.
CPC .......... *C08F 259/04* (2013.01); *C01B 32/942* (2017.08); *C07C 17/08* (2013.01);
(Continued)

(58) Field of Classification Search
CPC ...... C08F 114/06; C08F 259/04; C01B 31/32; C07C 17/08; C07C 17/25; C10H 15/00;
(Continued)

(56) References Cited

U.S. PATENT DOCUMENTS 2,779,804 A * 1/1957 Braconier ................ B01J 27/06
570/219

FOREIGN PATENT DOCUMENTS

CN 1116846 A 2/1996
CN 101336218 A 12/2008
(Continued)

OTHER PUBLICATIONS

Jiang et al., New Synthesis Process of Vinyl Chloride: 'Jiangzhong Method' Polyvinyl Chloride, No. 4, vol. 41, Apr. 25, 2013, 4 pages, English abstract enclosed.

*Primary Examiner* — William Cheung
(74) *Attorney, Agent, or Firm* — Bret E. Field; Bozicevic, Field & Francis LLP

(57) ABSTRACT

The present invention relates to a loop-route production method and system for polyvinyl chloride, and belongs to the intersecting fields of coal chemicals, polymer materials and chemical machinery. Limestone and carbon materials such as coal are reacted in an oxygen-enriched high temperature furnace to obtain calcium carbide and carbon monoxide, and then acetylene and carbon monoxide are respectively produced from calcium carbide and dichloroethane (obtaining ethylene, etc., through methanol or ethanol); both of the end products are combined to form a closed-loop; acetylene and dichloroethane are reacted to produce a vinyl chloride monomer, which is polymerized to obtain polyvinyl chloride. The system of the present invention mainly includes a device for pulverizing and mixing solid raw materials, a device for conveying solid materials, an oxygen-enriched calcium carbide furnace, an oxygen-
(Continued)

enriched air-blowing device, a tube-shell thermostatic reactor, a fixed bed tubular reactor, a fluidized bed reactor, an acetylene generator having a heat exchanger, a fixed bed reactor and a polymerization reactor. The present invention has the advantages of not only removing the dependence on oil resources during the production of polyvinyl chlorides, but also totally eliminating the mercury pollution.

10 Claims, 6 Drawing Sheets

(51) Int. Cl.
  *C08F 114/06*    (2006.01)
  *B01J 19/18*     (2006.01)
  *C08F 259/04*    (2006.01)
  *C07C 17/08*     (2006.01)
  *C07C 17/25*     (2006.01)
  *C10H 15/00*     (2006.01)
  *C10J 3/00*      (2006.01)
  *C01B 32/942*    (2017.01)

(52) U.S. Cl.
  CPC ............ *C07C 17/25* (2013.01); *C08F 114/06* (2013.01); *C10H 15/00* (2013.01); *C10J 3/00* (2013.01); *C10J 2300/0959* (2013.01); *C10J 2300/0996* (2013.01); *C10J 2300/1665* (2013.01)

(58) Field of Classification Search
  CPC ... C07C 17/25; C07J 21/06; C07J 17/08; C10J 2300/1665; C10J 2300/0996; C10J 2300/0959
  USPC .......................... 526/64, 344, 344.1; 422/132
  See application file for complete search history.

(56) References Cited

FOREIGN PATENT DOCUMENTS

| | | |
|---|---|---|
| CN | 102153085 A | 8/2011 |
| CN | 103408392 A | 11/2013 |
| CN | 103408393 A | 11/2013 |
| CN | 103408394 A | 11/2013 |

* cited by examiner

LOOP-ROUTE PRODUCTION METHOD AND SYSTEM FOR POLYVINYL CHLORIDE

This application is a national stage of PCT International Application No. PCT/CN2013/089907 filed on Dec. 19, 2013, which claims priority to and incorporates by reference the entire contents of China Patent Application No. 2013-10300933.8 filed on Jul. 17, 2013.

FIELD OF THE INVENTION

The present invention relates to a method for producing polyvinyl chloride and system (device) using the same, and more particularly, to a green loop-route synthesis method and system for producing polyvinyl chloride having the advantages in environmental protection, energy saving and high efficiency, which belong to the intersecting fields of coal chemicals, polymer materials and chemical machinery.

BACKGROUND OF THE INVENTION

Polyvinyl chloride (hereinafter referred to as "PVC" for short), one of the varieties having the largest production and sales volumes among polymer materials, is widely applied to a number of fields such as architecture, traffic, aviation and aerospace, national defense and military industry, etc., and plays a very important role in national economy and social development. Taking building materials as an example, PVC is more energy efficient during the process of production and usage in comparison with traditional materials, therefore PVC doors and windows have been popularized around developed western countries for a long time, and PVC ranks as highly recommended chemical building material for usage in China. Currently, there are mainly two production processes of PVC raw materials, i.e., "ethylene method" and "acetylene method". The route of "ethylene method", broadly used in the vast majority of countries around the world, has a limited development in China because of resource structure features of being "lack of oil, poor in gas and rich in coal". Instead, the "calcium carbide acetylene method", also named as "calcium carbide method", becomes a principal method in China, by means of which the produced PVC currently accounts for about 80% of the nationwide total output. The advantages and disadvantages of the above mentioned two traditional process routes for PVC production are respectively set forth in brief as follows:

In the process route for PVC production by calcium carbide method, coal, limestone and hydrogen chloride are used as raw materials. Coke and limestone are reacted to yield calcium carbide in high temperature melting state, and then calcium carbide is reacted with water to generate acetylene gas. Through an additional reaction between the resulting acetylene and hydrogen chloride, vinyl chloride (VCM) is generated, which is finally polymerized to obtain PVC, as shown in the process procedure thereof in FIG. 1. It is well-known that the production of calcium carbide involves in high energy consumption, and meanwhile the production of VCM monomer by calcium carbide method for PVC requires to use mercuric chloride catalyst as a catalyst, with about 1.2 kg of mercury catalyst consumed for producing per ton of PVC. Accordingly, for producing 10 million tons of PVC, about 12 thousand tons of catalyst will be consumed, which requires an input of 1.32 thousand tons of mercuric chloride. Thus, this route will cause problems of both high energy consumption and high contamination.

The process route for PVC production by ethylene method takes ethylene as raw material, and commonly uses ferric trichloride as a catalyst. Ethylene and chlorine are reacted in gas or liquid phase to generate dichloroethane, which is pyrolyzed in the pyrolyzer into vinyl chloride and hydrogen chloride, wherein the hydrogen chloride is recycled by reacting with ethylene and oxygen to generate dichloroethane again, and the vinyl chloride is polymerized to generate PVC. This method, named as ethylene-oxychlorination method, becomes the most widely used production method for PVC around the world, as shown in the process procedure thereof in FIG. 2. Ethylene method for PVC production has advantages in low contamination and relatively low energy consumption, but indispensably depends on petroleum resources, further involves in huge investment on equipments and high production cost.

SUMMARY OF THE INVENTION

It is an object of the present invention to provide a method for producing PVC, which has advantages in environmental protection, energy saving and high efficiency, and particularly, is not dependent on petroleum resources, but on rich-resourced coal and limestone to prepare PVC. In addition, the method solves the problem of mercury contamination and high energy consumption incurred with current calcium carbide method for PVC, so as to achieve green production for environmental protection and energy saving.

It is another object of the present invention to provide a method and system (device) for achieving the above mentioned preparation of PVC based on coal and limestone.

To achieve the above objects, in one aspect, the present invention provides a loop-route production method for polyvinyl chloride, a process for PVC production named as "loop-route method" for short, shown as the procedure thereof in FIG. 3, wherein the double-line arrow indicates a main process route presenting a closed-loop structure, which is capable of constructing a complete process by itself.

The process for PVC production via "loop-route method" according to the present invention is completely different from the open-loop mode production process of "calcium carbide method" or "ethylene method" in the prior art. The actual production is started from a high-temperature reaction furnace with oxygen-enriched calcium carbide, the oxygen-enriched calcium carbide composed of limestone plus carbon material plus oxygen gas as raw materials is reacted in the high-temperature reaction furnace to obtain calcium carbide as a solid product and CO syngas, and the subsequent process is divided into two branches: one branch (see leftward extension in FIG. 3) can obtain acetylene from calcium carbide; and the other (see rightward extension in FIG. 3) can firstly produce methanol or ethanol from CO syngas, and then produce dichloroethane by chloridization of methanol or ethanol; after that the two branches (the leftward and rightward two processes) are combined to form a closed loop after reactions, and acetylene and dichloroethane as two end products are reacted to produce vinyl chloride monomer (VCM), from which PVC can be obtained through existing technologies.

In the process of loop-route production method for polyvinyl chloride according to the present invention, there are multiple routes feasible to obtain dichloroethane from CO syngas, including not only obtaining dichloroethane from CO syngas via path of ethanol, but also obtaining dichloroethane by synthesizing ethylene via methanol-to-olefin (MTO) method. The detailed routes, for instance, consist in as follows: 1) ethanol is produced from CO syngas, and ethylene is produced from ethanol and directly chloridized or oxychloridized to obtain dichloroethane; 2) ethanol is produced from CO syngas and directly chloridized to obtain dichloroethane; 3) methanol is produced from CO syngas, acetic acid is produced from methanol, ethanol is produced from acetic acid, and ethylene is produced from ethanol and directly chloridized or oxychloridized to obtain dichloroethane; 4) methanol is produced from CO syngas, and ethylene is synthesized through methanol-to-olefin (MTO) method to further obtain dichloroethane; and 5) methanol is prepared from carbon monoxide, methane chloride is prepared from methanol and hydrogen chloride and dehydrogenized to prepare dichloroethane. All of these are commonly known mature technologies.

According to the loop-route production method for polyvinyl chloride of the present invention, each production unit of the process may further acquire or be complemented with desired products from external, or provide intermediate products to external as per actual requirement.

According to the production method for PVC via "loop-route method" of the present invention, compared with traditional "calcium carbide method", the reaction process thereof avoids the path of the reaction between acetylene and hydrogen chloride using mercury accelerant (catalyst) to generate vinyl chloride, instead, it allows the reaction between acetylene and dichloroethane to produce vinyl chloride, during which mercury-free catalyst (usually no-polluting barium chloride catalyst) can be used as a novel catalyst, thereby thoroughly solving the environmental problem associated with mercury-contamination in the industry of polyvinyl chloride via "calcium carbide method".

The present invention further provides a production system for PVC via "loop-route method", mainly including a device for pulverizing (crushing) and mixing solid raw materials, a device for conveying solid materials, an oxygen-enriched calcium carbide furnace, an oxygen-enriched air-blowing device, a tube-shell thermostatic reactor, a fixed bed tubular reactor, a fluidized bed reactor, an acetylene generator having a heat exchanger, a fixed bed reactor and a polymerization reactor. A homogeneous mixture of limestone powder and carbon material powder is delivered into the oxygen-enriched calcium carbide furnace by the device for pulverizing and mixing raw materials and the device for conveying solid materials. Starting from the oxygen-enriched calcium carbide furnace, the production process is divided into two branches: in one branch, the oxygen-enriched calcium carbide furnace is sequentially connected with the acetylene generator having a heat exchanger and the fixed bed reactor for producing acetylene, and in the other branch, the oxygen-enriched calcium carbide furnace is sequentially connected with the tube-shell thermostatic reactor, the fixed bed tubular reactor and the fluidized bed reactor for producing dichloroethane. After that the two branches are combined at the fixed bed reactor to complete the preparation of vinyl chloride monomer, and the fixed bed reactor is connected with the polymerization reactor, so that materials therein are reacted to finally obtain PVC.

According to the production system for PVC via "loop-route method" of the present invention, the oxygen-enriched calcium carbide furnace is a shaft furnace, into which a homogeneous mixture of limestone powder and carbon material powder under strict proportioning requirement (i.e., in a proportion desired for achieving complete reaction) is delivered by a device for pulverizing and mixing solid raw materials and a device for conveying solid materials. The oxygen-enriched calcium carbide furnace is provided with a plasma ignition combustion-supporting device and a furnace temperature detection and control device, and a solid material inlet and an oxygen inlet. Oxygen is feed into the oxygen-enriched calcium carbide furnace by an oxygen-enriched air-blowing device through the gas inlet. The solid materials are reacted stably at a predetermined reaction temperature under the conditions under which oxygen is involved (the optimized process conditions, such as reaction temperature and the conditions under which oxygen is involved can be selected according to the prior art which the technical field belongs to). The shaft furnace of the oxygen-enriched calcium carbide furnace is provided with a first gas outlet of syngas at upper portion thereof, and a solid material outlet for discharging calcium carbide at bottom portion thereof. The materials discharged from the oxygen-enriched calcium carbide furnace pass into the next step of procedure in two routes respectively. Since the materials fed into the oxygen-enriched calcium carbide furnace by the production system for PVC via "loop-route method" according to the invention are not merely powder coal fuel, but the homogeneous mixture of limestone powder and coal powder under strict proportioning requirement, the material supplying device, on the basis of thermal power boiler feeding system, is further provided with a specialized metering device for supplying and mixing materials controlled by a computer, which, together with detection elements for critical process parameters such as furnace temperature, yield and the like, constitutes a closed-loop system, so as to provide equipment support for product quality control and process optimization. In the specific implementation, the feeding ratio between limestone and carbon powder can be adjusted depending on the contents of effective components in the raw materials. According to common test results, the ratio between limestone and carbon powder is 1:1 to 3. The higher the amount of carbon powder is, the more the heat is provided, and the more sufficiently the limestone reacts. If an electric furnace is employed, the amount of carbon powder (material) used can be appropriately reduced.

According to the production system for PVC via "loop-route method" of the present invention, calcium carbide exits from the solid material outlet of the oxygen-enriched calcium carbide furnace, and the acetylene generator having a heat exchanger is provided with a first material inlet, a second gas outlet and a first material outlet, and sequentially connected to a screw conveyer, which can be a ceramic screw conveyer, and a post-treatment device, wherein the calcium carbide enters into the acetylene generator having a heat exchanger through the first material inlet, and reacted with water to generate acetylene, which is discharged through the second gas outlet as starting material for the next step of reaction. Meanwhile, the residual heat is exported and utilized. The carbide slag discharged from the first material outlet is converted to construction materials through said screw conveyer and post-treatment device, so as to achieve green production without "three wastes" (waste gas, waste water, industrial residual) during the whole process.

According to the production system for PVC via "loop-route method" of the present invention, syngas discharged from the first gas outlet one at the upper portion of the oxygen-enriched calcium carbide furnace enters into the tube-shell thermostatic reactor, and is fully reacted in the shell thermostatic reactor to obtain ethanol under the condition of making full use of the residual heat. The ethanol is passed into the fixed bed tubular reactor and reacted to prepare ethylene therein (alternatively, the reaction starts from methanol to obtain ethylene via an ethanol route), and ethylene is chloridized through a fluidized bed reactor to prepare dichloroethane as starting material for the next step of reaction. The fixed bed tubular reactor is provided with an ethanol inlet, an ethylene outlet, a first heat carrying medium inlet and a first heat carrying medium outlet, and the fluidized bed reactor is provided with an ethylene inlet, dichloroethane outlet, a second heat carrying medium inlet and a second heat carrying medium outlet, wherein the heat carrying medium is imported into the fixed bed tubular reactor and the fluidized bed reactor through the first heat carrying medium inlet and the second heat carrying medium inlet respectively, so as to provide the reaction with necessary heat energy, and then discharged from the first heat carrying medium outlet and the second heat carrying medium outlet.

According to the production system for PVC via "loop-route method" of the present invention, the fixed bed reactor is provided with a second material inlet, a third material inlet and a second material outlet, wherein the acetylene prepared by the acetylene generator having a heat exchanger enters into the fixed bed reactor through the second gas outlet and the second material inlet, the dichloroethane from the fluidized bed reactor enters into the fixed bed reactor through the third material inlet, and the acetylene and dichloroethane are reacted to produce vinyl chloride monomers (VCM) under the action of a novel mercury-free catalyst in the fixed bed reactor. The resulting vinyl chloride monomers enter into a polymerization reactor through the second material inlet and polymerized to obtain the suspended particulate matter of PVC, which can be processed through a separation and drying equipment to acquire packaged PVC powder products, or can be further processed to achieve in-mold or out-of-mold laminated calculus mixing granulation of PVC polymer melts by means of a screw extrusion device driven by a driving unit and a device for in-mold or out-of-mold laminated calculus mixing granulation, to completely expand PVC aggregates, so as to obtain high-strength, high-transparency and high-barrier-performance PVC products with high added value. The novel catalyst used in the reaction is a mercury-free catalyst, and generally active substances such as barium chloride, stannic chloride, and chlorides of rare earth elements or other noble metals, all of which pertain to the prior art pertinent to the technical field.

In the present invention, the process conditions which are not detailed above can be all performed according to the prior art pertinent to the technical field.

The beneficial effects from the production system and method for PVC via "loop-route method" of the present invention can be summarized as follows:

1) compared with traditional "calcium carbide method", the "loop-route method" of the present invention is not only superior in abundant raw materials, but also avoids use of mercury catalyst, which is replaced with mercury-free catalyst such as barium chloride as a novel catalyst, such that the environmental problem resulting from mercury-contamination facing the industry of polyvinyl chloride can be more thoroughly solved over the solution using low mercury catalyst developed broadly in the prior art;

2) compared with "ethylene method", the "loop-route method" of the present invention is not only superior in environmental protection, but also free from dependence on petroleum resources. Moreover, said method only retains the most simple one among the three units of the "ethylene method", i.e., chloridization of ethylene to produce dichloroethane, so as to leave out the dichloroethane pyrolysis unit with high energy consumption and the oxychlorination unit requiring complicated equipments, thereby not only dramatically reducing the investment on equipments, but also rendering the production process more energy-efficient;

3) the "loop-route method" of the present invention adopts a closed-loop process route. At the bottom portion of the smelting furnace (see leftward extended process in FIG. 3), the solid resultant carbide slag produced after the preparation of acetylene from calcium carbide can be used to produce cement, and at the top portion of the smelting furnace (see rightward extended process in FIG. 3), CO syngas participates completely in the subsequent reactions, thereby not only substantially decreasing the discharge of CO, but also shortening the procedure and self-offsetting partial energy of endothermal reactions and exothermal reactions, so as to dramatically reduce the energy consumption during production, which presents outstanding advantages of environmental protection and energy saving over the prior art;

4) the "loop-route method" of the present invention is a green production process, and meanwhile, each production unit of the process may further acquire desired products from external, or provide intermediate products to external as per actual requirement. For instance, at the step of ethanol, bioethanol, which is produced from biomass raw materials or carbon monoxide raw materials through biochemical methods, can be provided from external, and at the step of acetylene, equivalent of acetylene raw materials can be acquired through methods using shale gas, natural gas or coal plasma for example, so as to achieve multi-functional and multi-effective co-production operation;

5) an intelligently-controlled and high-efficient oxygen-enriched calcium carbide furnace is employed as a generator for calcium carbide and CO, so as to allow improved conversion of target products and availability of raw materials;

6) a package plant for utilization of residual heat from an acetylene generator having a function of high efficient heat exchange is provided, such that a great quantity of heat energy encompassed in calcium carbide exported from shaft furnace and that released from the reaction of carbide with water to generate acetylene can be cycled to use, thereby saving energy resources and lowering production cost;

7) the application of the unit for nano-laminated calculus mixing granulation can substantially improve the operational performance of PVC products and increase their added values;

8) the production process for PVC via "loop-route method" of the present invention can tremendously improve natural balance ability of materials, avoid the problem of redundant intermediate products and have advantages in low energy saving and high efficiency, thereby allowing both of reduced production cost and environmental protection.

According to the production system and method for PVC via "loop-route method" of the present invention, the self-offsetting of partial energy of endothermal reactions and exothermal reactions is realized during the process of chemical reactions inside the whole system, and enhanced heat transfer and mass transfer and high-efficiency reaction are inventively achieved through integration of system equipments. The core devices of said system provide multiple supporting measures for lean production, such as refining and homogeneously mixing particles of raw materials, forming closed loop for reaction material flow, strictly controlling reaction conditions, recycling residual heat energy during production, thereby achieving a comprehensive effect of environmental protection, energy saving and high efficiency.

| | |
|---|---|
| 11 - device for pulverizing and mixing solid raw materials, | 12 - device for conveying solid materials, |
| 13 - oxygen-enriched calcium carbide furnace, | 14 - oxygen-enriched air-blowing device, |
| 15 - solid material inlet, | 16 - solid material outlet, |
| 17 - gas inlet, | 18 - first gas outlet, |
| 21 - acetylene generator having a heat exchanger, | 22 - first material inlet, |
| 23 - second gas outlet, | 24 - first material outlet, |
| 25 - ceramic screw conveyer, | 26 - post-treatment device, |
| 31 - a tube-shell thermostatic reactor, | 32 - fixed bed tubular reactor, |
| 33 - a fluidized bed reactor, | 34 - first heat carrying medium inlet, |
| 35 - first heat carrying medium outlet, | 36 - second heat carrying medium inlet, |
| 37 - second heat carrying medium outlet, | 41 - fixed bed reactor, |
| 42 - reactor, | 43 - second material inlet, |
| 44 - third material inlet, | 45 - second material outlet, |
| 51 - screw extrusion device, | 52 - device for in-mold or out-of-mold laminated calculus mixing granulation, |
| 53 - driving unit, | 27 - natural gas processing equipment, |
| 38 - bioethanol processing equipment for. | |

DETAILED DESCRIPTION OF THE EMBODIMENTS

The technical solutions of the present invention will now be further detailedly illustrated in conjunction with examples and figures, in order to more clearly understand the technical features, objectives and effects of the present invention, but the invention is not limited thereto in any way.

Figure 6:
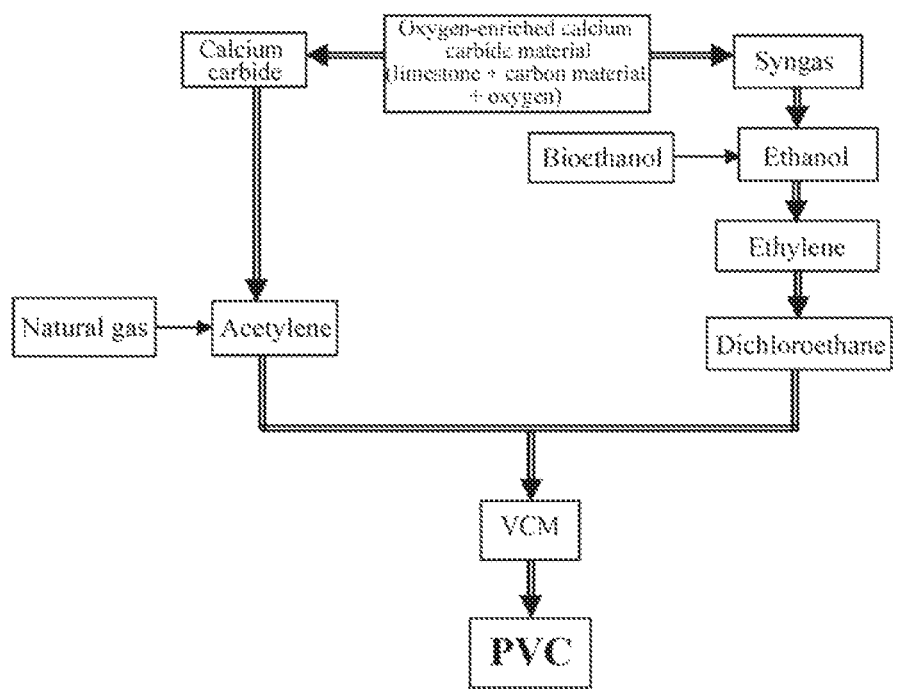
FIG. 6 is a flowchart of the production process for PVC via extended loop-route method according to another particular embodiment of the present invention.
Figure 7:
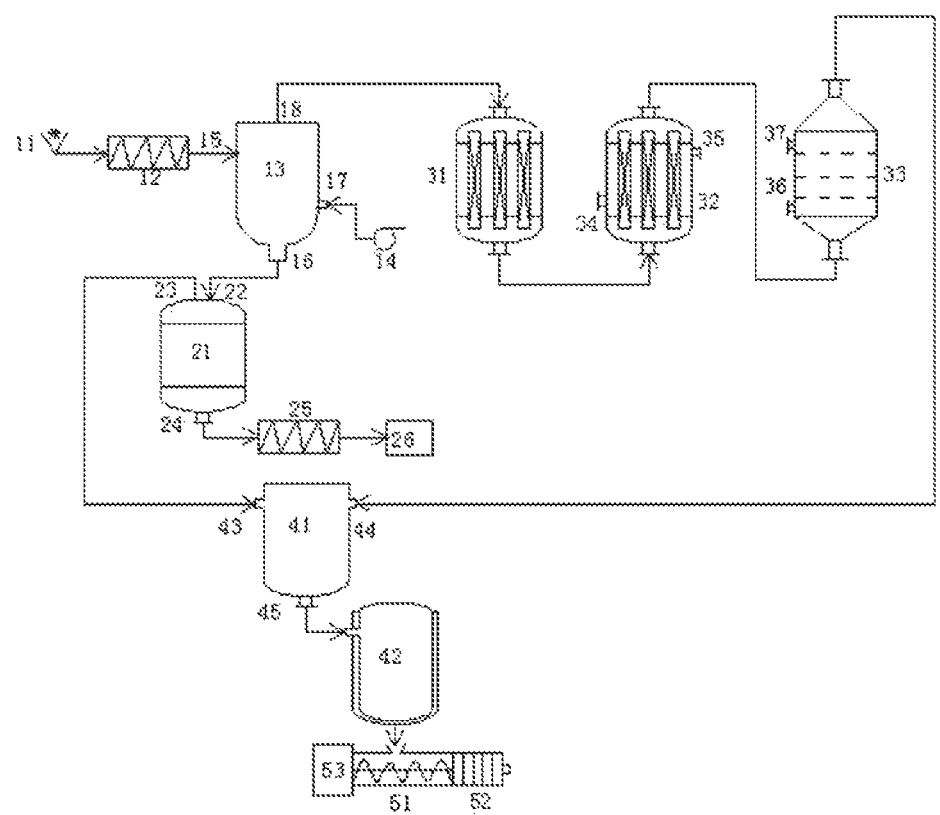
FIG. 7 is a schematic diagram of the production system for PVC via basic loop-route method according to the loop-route production system for polyvinyl chloride of the present invention.

The production system for polyvinyl chloride via basic loop-route method of the present invention applies a "loop-route" production process for PVC. As shown in FIGS. 6 and 7, the system mainly comprises a device for pulverizing and mixing solid raw materials 11, a device for conveying solid materials 12, an oxygen-enriched calcium carbide furnace 13, an oxygen-enriched air-blowing device 14, a tube-shell thermostatic reactor 31, a fixed bed tubular reactor 32, a fluidized bed reactor 33, an acetylene generator having a heat exchanger 21, a fixed bed reactor 41 and a reactor 42. A homogeneous mixture of limestone powder and carbon material powder is delivered by the device for pulverizing and mixing solid raw materials 11 and the device for conveying solid materials 12 into the oxygen-enriched calcium carbide furnace 13. Starting from the oxygen-enriched calcium carbide furnace 13, the production process is then divided into two branches: in one branch, the oxygen-enriched calcium carbide furnace 13 is sequentially connected with the acetylene generator having a heat exchanger 21 and the fixed bed reactor 41 for producing acetylene, and in the other branch, the oxygen-enriched calcium carbide furnace 13 is sequentially connected with the tube-shell thermostatic reactor 31, the fixed bed tubular reactor 32 and the fluidized bed reactor 33 for producing dichloroethane. After that the two branches are combined at the fixed bed reactor 41 to complete the preparation of vinyl chloride monomer. The fixed bed reactor 41 is connected with a polymerization reactor 42, so that materials therein are reacted to finally prepare PVC. The invention is now illustrated according to examples of two methods and two systems in conjunction with the production process.

Example 1: Production Process for PVC Via Basic "Loop-Route" Method (Via Ethanol)

Figure 1:
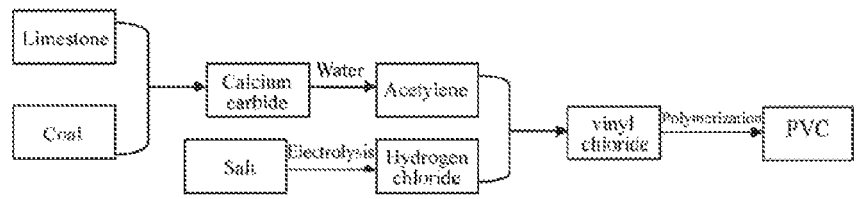
FIG. 1 is a schematic diagram of the process procedure (open loop) according to calcium carbide method for PVC production in the prior art.
Figure 2:
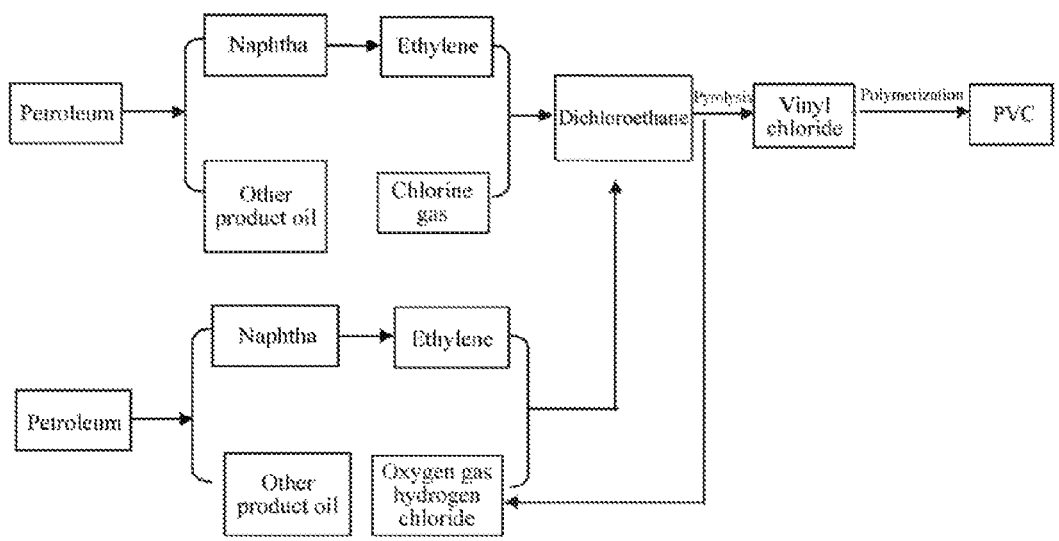
FIG. 2 is a schematic diagram of the process procedure (open loop) according to ethylene method for PVC production in the prior art.
Figure 3:
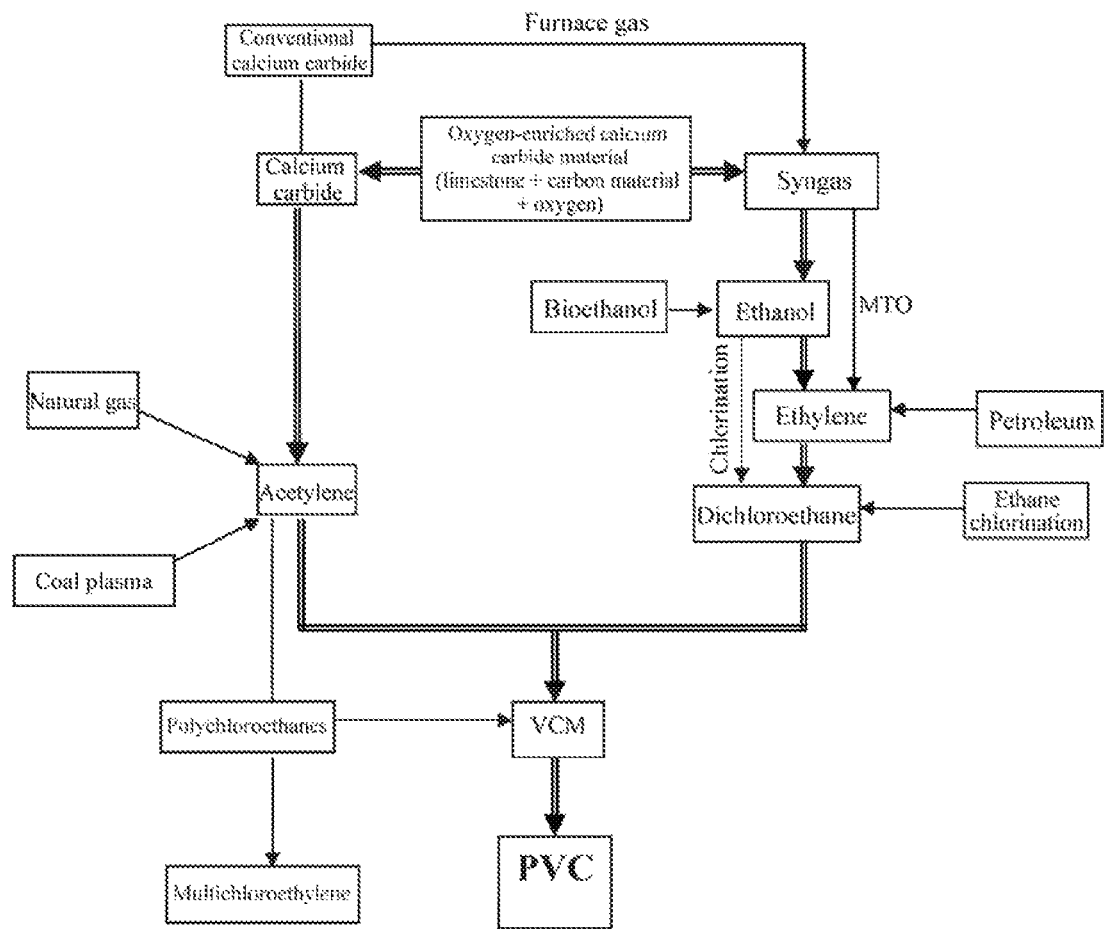
FIG. 3 is a schematic diagram of the process procedure (closed loop) according to the loop-route production method for polyvinyl chloride of the present invention.
Figure 4:
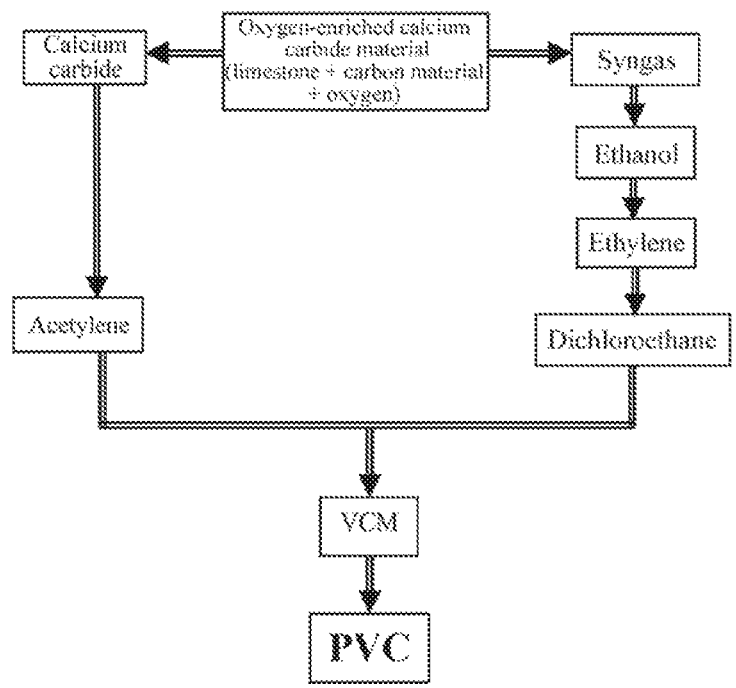
FIG. 4 is a flowchart of the production process for PVC via basic loop-route method according to one particular embodiment of the present invention.

This example relates to a basic loop-route method process procedure for polyvinyl chloride via an ethanol route, as shown in FIG. 4. The specific embodiment of process and equipments is illustrated as follows:

1) Start: a shaft furnace was used as the oxygen-enriched calcium carbide furnace. Limestone powder and coal powder were prepared by a device for preprocessing and mixing raw materials. The homogeneous mixture of limestone powder and coal powder under strict proportioning requirement was fed into the furnace and reacted stably with oxygen under the determined optimized process conditions. CO syngas was discharged from the upper portion of the furnace, and calcium carbide was exported from the bottom portion thereof, as shown in FIG. 4, both of which were passed into the next step of procedure from the left and right sides respectively. The strict proportioning requirement refers to the proportioning requirement on starting materials desired for achieving complete reaction, which is specifically determined depending on test results of active ingredients of starting materials. The optimized process conditions can be selected under any feasible operation in the prior art. The stable reaction with oxygen was usually performed under the condition of 800° C. to 1,200° C.

2) Left route: calcium carbide was exported from the shaft furnace reactants, and reacted with water through a high-efficient acetylene generator by using residual heat to generate acetylene as starting material for the next step of reaction, and meanwhile the residual heat was fully used, and carbide slag was converted into construction materials through a conveyer and post-treatment device.

3) Right route: the CO syngas discharged from the upper portion of the shaft furnace was reacted to obtain ethanol under the condition of making full use of the residual heat, and then the ethanol was dehydrated to prepare ethylene, which was further chloridized to prepare dichloroethane (the ethanol can also be chloridized directly to prepare dichloroethane) as starting material for the next step of reaction. More specifically, CO syngas can be reacted to obtain ethanol under the action of rhodium catalyst at temperatures from 200° C. to 300° C. that was maintained by the residual heat released from the heat exchanger, then the ethanol was dehydrated to produce ethylene under the action of $Al_2O_3$ catalyst at 300° C. to 400° C., after that the ethylene was further chloridized or oxychloridized to obtain dichloroethane (the ethanol can also be chloridized directly to prepare dichloroethane) as starting material for the next step of reaction.

4) Combination: the acetylene prepared from the left route and the dichloroethane prepared from the right route were reacted by means of existing techniques to produce vinyl chloride monomers, which were subsequently imported into a polymerization reactor and polymerized to obtain PVC suspended matters. The PVC suspended matters can be processed through a separation and drying equipment to acquire PVC powder products, and can further be processed to achieve in-mold or out-of-mold laminated calculus mixing granulation of PVC polymer melts by means of the equipments of the present invention, to fully expand PVC aggregates, so as to obtain high-performance and high-added-value PVC products.

More specifically, the acetylene prepared from the left route and the dichloroethane prepared from the right route were reacted under the action of mercury-free catalyst such as barium chloride or stannic chloride at temperatures from 200° C. to 300° C. to produce vinyl chloride monomer, which was imported into a polymerization reactor and polymerized through initiators such as peroxide at temperatures from 50° C. to 70° C. to obtain PVC suspended particulate matter. The PVC suspended particulate matter can be processed through a separation and drying equipment to give PVC powder products, and can further be processed to achieve in-mold or out-of-mold laminated calculus mixing granulation of PVC polymer melts by means of the equipments of the present invention, to fully expand PVC aggregates, so as to obtain high-performance and high-added-value PVC products.

In the above process of this example, mercury-free catalysts, such as stannic chloride, chlorides of rare earth or other noble metals, can be used as catalyst, thereby preventing the contamination problem resulting from mercury catalyst adopted in the traditional industry of polyvinyl chloride.

Example 2: Production Process for PVC Via Basic "Loop-Route" Method (Preparation of Ethanol Via Methanol)

This example relates to a basic loop-route method process procedure for polyvinyl chloride via a methanol route, and a transition unit associated with preparation of ethanol via methanol is added to the procedure as shown in FIG. 4. The specific embodiment of process and equipments is illustrated as follows:

1) Start: a shaft furnace was used as the oxygen-enriched calcium carbide furnace. Limestone powder and coal powder were prepared by a device for preprocessing and mixing raw materials. The homogeneous mixture of limestone powder and coal powder was fed into the furnace under proportioning requirement on starting materials desired for achieving complete reaction depending on test results of active ingredients of starting materials, and reacted stably with oxygen under the determined condition of 1,200° C. to 2,000° C. The CO syngas was discharged from the upper portion of the furnace, and calcium carbide was exported from the bottom portion thereof, both of which were passed into the next step of procedure from left and right sides respectively, as shown in FIG. 4.

2) Left route: the calcium carbide was exported from the shaft furnace reactants, and reacted with water through a high-efficient acetylene generator by using residual heat to generate acetylene as starting material for the next step of reaction, and meanwhile the residual heat was fully used, and carbide slag was converted into construction materials through a conveyer and post-treatment device.

3) Right route: the CO syngas discharged from the upper portion of the shaft furnace was reacted under the pressure condition of 9.8 MPa to 12 MPa at 240° C. to 270° C. maintained by the residual heat released from the heat exchanger to obtain methanol, which was subsequently reacted using tertiary organophosphine-cobalt hydrocarbonyl catalyst under the pressure condition of 9.8 MPa to 14.7 MPa at 200° C. to obtain ethanol. The methanol can also be reacted to prepare acetic acid in presence of rhodium catalyst under the condition of 150° C. to 220° C., and the acetic acid was then reacted in presence of platinum or tin catalyst to obtain ethanol. Then, the ethanol was dehydrated to produce ethylene under the action of $Al_2O_3$ at 300° C. to 400° C., after that ethylene was further chloridized or oxychloridized to obtain dichloroethane (the ethanol can also be chloridized directly to prepare dichloroethane) as starting material for the next step of reaction.

4) Combination: the acetylene prepared from the left route and the dichloroethane prepared from the right route were reacted under the action of mercury-free catalyst such as barium chloride or stannic chloride at temperatures from 200° C. to 300° C. to produce vinyl chloride monomers, which were subsequently imported into a polymerization reactor and polymerized through initiators such as peroxide at temperatures from 50° C. to 70° C. to obtain PVC suspended particulate matters. The PVC suspended particulate matters were processed through a separation and drying equipment to give PVC powder products, and can further be processed to achieve in-mold or out-of-mold laminated calculus mixing granulation of PVC polymer melts by means of the equipments of the present invention, to fully expand PVC aggregates, so as to obtain high-performance and high-added-value PVC products.

Example 3: Production Process for PVC Via Basic "Loop-Route" Method (Preparation of Methane Chloride Via Methanol)

Figure 5:
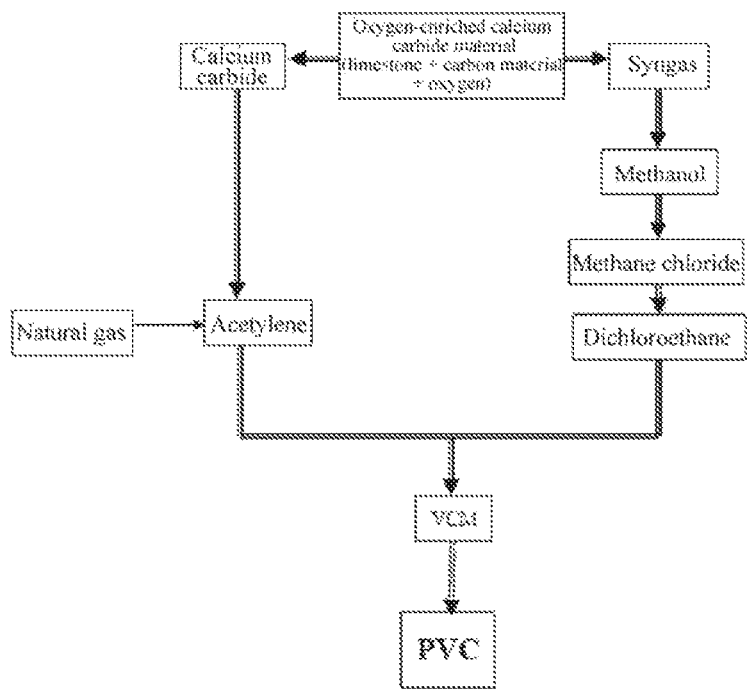
FIG. 5 is a flowchart of the production process for PVC via basic loop-route method according to another particular embodiment of the present invention.

This example relates to another embodiment of a basic loop-route method process procedure for polyvinyl chloride via a methanol route, as shown in FIG. 5, in which the right route of the procedure as shown in FIG. 4 is converted into the route of preparation of methanol from CO syngas and then passing through methane chloride to dichloroethane. The specific embodiment of process and equipments is illustrated as follows:

1) Start: a shaft furnace was used as the oxygen-enriched calcium carbide furnace. Limestone powder and coal powder were prepared by a device for preprocessing and mixing raw materials. The homogeneous mixture of limestone powder and coal powder was fed into the furnace under proportioning requirement on starting materials desired for achieving complete reaction depending on test results of active ingredients of starting materials, and reacted stably with oxygen under the determined condition of 1,200° C. to 2,000° C. The CO syngas was discharged from the upper portion of the furnace, and calcium carbide was exported from the bottom portion thereof, both of which were passed into the next step of procedure from left and right sides respectively, as shown in FIG. 5.

2) Left route: the calcium carbide was exported from the shaft furnace reactants, and reacted with water through a high-efficient acetylene generator by using residual heat to generate acetylene as starting material for the next step of reaction, and meanwhile the residual heat was fully used, and carbide slag was converted into construction materials through a conveyer and post-treatment device.

3) Right route: the CO syngas discharged from the upper portion of the shaft furnace was reacted under the pressure condition of 9.8 MPa to 12 MPa at 240° C. to 270° C. maintained by the residual heat released from the heat exchanger to obtain methanol, which was reacted to obtain methane chloride by gas phase method (with addition of chlorine gas under the condition of 300° C. to 350° C.) or liquid phase method (with addition of hydrochloric acid under the condition of 130° C. to 150° C.), after that the methane chloride was reacted in presence of catalyst of oxides of ferrum or stibium at 400° C. to 450° C. to obtain dichloroethane as starting material for the next step of reaction.

4) Combination: the acetylene prepared from the left route and the dichloroethane prepared from the right route were reacted under the action of mercury-free catalyst such as barium chloride or stannic chloride at temperatures from 200° C. to 300° C. to produce vinyl chloride monomer, which were subsequently imported into a polymerization reactor and polymerized through initiators such as peroxide at temperatures from 50° C. to 70° C. to obtain PVC suspended particulate matters. The PVC suspended particulate matters were processed through a separation and drying equipment to give PVC powder products, and can further be processed to achieve in-mold or out-of-mold laminated calculus mixing granulation of PVC polymer melts by means of the equipments of the present invention, to fully expand PVC aggregates, so as to obtain high-performance and high-added-value PVC products.

Example 4: Production Process for PVC Via Extended "Loop-Route" Method (Natural Gas or Shale Gas and Starting Materials of Bioethanol)

The extended loop route for polyvinyl chloride as described below in this example is designed to set open window in the intermediate step of the basic loop route to allow addition of intermediate starting materials from external, in order to adapt to diversity of resource structures in various countries and regions. As shown in FIG. 6, the specific embodiment is illustrated as follows:

In the above basic loop route process procedure as shown in FIG. 4, in case that acetylene prepared from the left route can be conveniently supplemented or replaced with natural gas or shale gas depending on actual resource conditions in different regions, acetylene can be produced by means of commonly known techniques, such as natural gas (methane) partial oxidation process, and the right route can be complemented with supporting equipment for bioethanol from natural resource.

Example 5: Basic "Loop-Route" Method Production System

This example provides a basic loop-route method production system for polyvinyl chloride and the corresponding production process thereof, as shown in FIG. 7. The specific embodiment is illustrated as follows:

1) Start: an oxygen-enriched calcium carbide furnace 13 was a shaft furnace, into which a homogeneous mixture of limestone powder and carbon material powder under strict proportioning requirement obtained by a device for pulverizing and mixing solid raw materials 11 was fed through a device for conveying solid materials 12. The oxygen-enriched calcium carbide furnace 13 was provided with a solid material inlet 15 and an oxygen gas inlet 17, wherein oxygen was charged therein by an oxygen-enriched air-blowing device 14 through the gas inlet 17 and solid materials were reacted stably under the conditions of determined optimized process conditions and oxygen involved in. The shaft furnace of the oxygen-enriched calcium carbide furnace 13 was provided with a first gas outlet 18 for syngas at the upper portion thereof, and a solid material outlet 16 for exporting calcium carbide at the bottom portion thereof. The materials exported from the oxygen-enriched calcium carbide furnace 13 passed into the next step of procedure in two routes respectively. As the materials delivered into the oxygen-enriched calcium carbide furnace by the device of the present invention are not merely fuel braize, but the homogeneous mixture of limestone powder and carbon material powder under strict proportioning requirement, the material supplying device, on the basis of thermal power boiler feeding system, can be further provided with a specialized metering device for supplying and mixing materials controlled by computer (feasibly using a device for supplying and mixing materials in the prior art as part of the oxygen-enriched calcium carbide furnace 13, not separately shown in FIG. 7), which, together with detection elements for critical process parameters such as furnace temperature, yield and the like, constitutes a closed-loop system, so as to provide equipment support for product quality control and process optimization.

2) Left route: calcium carbide was exported from the solid material outlet 16 of the oxygen-enriched calcium carbide furnace 13. The acetylene generator having a heat exchanger 21 was provided with a first material inlet 22, a second gas outlet 23 and a first material outlet 24, wherein the calcium carbide entered into the acetylene generator having a heat exchanger 21 through the first material inlet 22, and reacted with water to generate acetylene, which is discharged through the second gas outlet 23 as starting material for the next step of reaction. The heat exchanger, as a high temperature fluid heat pipe heat exchanger with specified working medium selected upon reaction temperature, can make full use of a great quantity of heat energy encompassed in calcium carbide exported from the shaft furnace and that released from the reaction of calcium carbide with water to generate acetylene. The heat energy was available to preheat reaction materials fed into the oxygen-enriched calcium carbide furnace 13 or oxygen-enriched gas (for instance oxygen) blown by the oxygen-enriched air-blowing device 14, and meanwhile the residual heat was fully used and the carbide slag discharged through the first material outlet 24 is converted to construction materials through a ceramic screw conveyer 25 and a post-treatment device 26.

3) Right route: the CO syngas discharged from the first gas outlet 18 at the upper portion of the oxygen-enriched calcium carbide furnace 13 entered into a tube-shell thermostatic reactor 31, in which the CO syngas was reacted to obtain ethanol under the condition of making full use of the residual heat at 250° C. to 300° C. The ethanol entered into a fixed bed tubular reactor 32, in which ethylene was prepared from ethanol, and the ethylene was chloridized through a fluidized bed reactor 33 to prepare dichloroethane as starting material for the next step of reaction. The fixed bed tubular reactor 32 was provided with an ethanol inlet, an ethylene outlet, a first heat carrying medium inlet 34 and a first heat carrying medium outlet 35, and the fluidized bed reactor 33 was provided with an ethylene inlet, a dichloroethane outlet, a second heat carrying medium inlet 36 and a second heat carrying medium outlet 37, wherein the heat carrying medium was imported into the fixed bed tubular reactor 32 and the fluidized bed reactor 33 through the first heat carrying medium inlet 34 and the second heat carrying medium inlet 36 respectively, so as to provide necessary heat energy for reaction, and then discharged from the first heat carrying medium outlet 35 and the second heat carrying medium outlet 37.

4) Combination: acetylene prepared from the acetylene generator having a heat exchanger 21 at the left route entered into a fixed bed reactor 41 through the second gas outlet 23 and the second material inlet 43, and dichloroethane prepared from the right route entered into the fixed bed reactor 41 from the fluidized bed reactor 33 through the third material inlet 44. The acetylene and the dichloroethane were reacted in the fixed bed reactor 41 to produce vinyl chloride monomers, which were imported into a polymerization reactor 42 through a second material outlet 45 and polymerized to obtain PVC suspended particulate matters. The PVC suspended particulate matters were processed through a separation and drying equipment to acquire packaged PVC powder products, and can be further processed to achieve in-mold or out-of-mold laminated calculus mixing granulation of PVC polymer melts by means of a screw extrusion device 51 driven by a driving unit 53 and a device for in-mold or out-of-mold laminated calculus mixing granulation 52, to fully expand PVC aggregates, so as to obtain high-performance and high-added-value PVC products.

Example 6: Extended Loop-Route Method Production System

Figure 8:
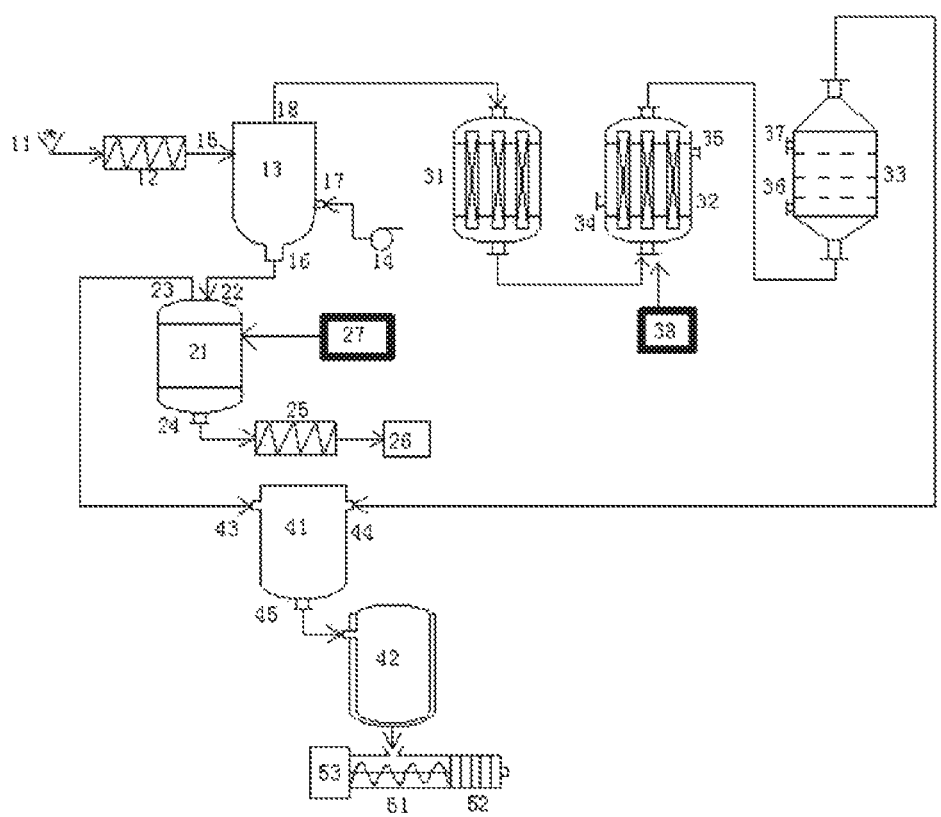
FIG. 8 is a schematic diagram of the production system for PVC via extended loop-route method according to the loop-route production system for polyvinyl chloride of the present invention.

This example provides an extended loop-route production system for polyvinyl chloride and the corresponding process thereof, which are designed to set open window in the intermediate step of the basic loop route, to allow addition of intermediate starting materials from external, in order to extend the loop-route production system for polyvinyl chloride of the present invention and render it adaptive to the diversity of resource structures in various countries and regions. Referring to FIG. 8, the specific embodiment in accordance with the extended loop-route production system is illustrated as follows:

In the basic loop-route process system as shown in FIG. 7, at the units for utilization of residual heat from the acetylene generator and post-treatment of carbide slag, a natural gas processing equipment 27 was additionally provided adjacent to the acetylene generator having a heat exchanger 21, for preparing acetylene. As shown in FIG. 8, the natural gas processing equipment 27 was interconnected with the acetylene generator having a heat exchanger 21 through the first material inlet 22 or directly. Accordingly, at the unit for preparing dichloroethane from the syngas, a bioethanol processing equipment 38 was additionally provided adjacent to the fixed bed tubular reactor 32 in which ethanol was dehydrated to produce ethylene. The bioethanol processing equipment 38 was interconnected with the material inlet of the fixed bed tubular reactor 32. In case that acetylene can be conveniently supplemented with resource of natural gas, acetylene prepared through the natural gas processing equipment 27 was fed into the acetylene generator having a heat exchanger 21 or the fixed bed reactor 41. To match up thereto, ethanol prepared from CO syngas can be supplemented with bioethanol from natural resource wherein, the bioethanol was processed through the bioethanol processing equipment 38 to produce ethanol, which was then fed into the fixed bed tubular reactor 32, so as to achieve material balance.

What is claimed is:

1. A loop-route production method for polyvinyl chloride, characterized in that, comprising:
   1) start: starting from an oxygen-enriched calcium carbide high temperature reaction furnace, reacting limestone, carbon material and oxygen as basic starting materials in the high temperature furnace to obtain solid resultant calcium carbide and carbon monoxide syngas;
   2) first route: producing acetylene from the calcium carbide;
   3) second route: producing dichloroethane from the carbon monoxide syngas; and
   4) combination: combining acetylene from the first route and dichloroethane from the second route to form a closed loop, reacting the acetylene with the dichloroethane to produce vinyl chloride monomers, and finally polymerizing the vinyl chloride monomers to obtain polyvinyl chloride.

2. The loop-route production method for polyvinyl chloride according to claim 1, characterized in that, mercury-free catalyst is used during the reaction process.

3. The loop-route production method for polyvinyl chloride according to claim 1, characterized in that, producing dichloroethane from the carbon monoxide syngas consists in:
   producing dichloroethane from the carbon monoxide syngas via reactions from methanol to ethanol and from the ethanol to ethylene sequentially, or
   producing dichloroethane directly via a reaction from methanol to olefin (MTO) from the carbon monoxide syngas.

4. The loop-route production method for polyvinyl chloride according to claim 1, characterized in that, carbide slag at a bottom portion of the furnace, as residue from preparation of the acetylene from the solid resultant calcium carbide, is used for cement production.

5. The loop-route production method for polyvinyl chloride according to claim 1, characterized in that, each production unit can acquire or be supplemented with desired products from external, or provide intermediate products to external.

6. The loop-route production method for polyvinyl chloride according to claim 5, characterized in that, acetylene used as complementary or substituted starting material is prepared by a partial oxidation process from natural gas or shale gas, and accordingly ethanol is produced from biomass or carbon monoxide as raw materials by a biological fermentation process.

7. A system for realizing the loop-route production method for polyvinyl chloride according to claim 1, characterized in that, the system mainly comprises:
   a device for pulverizing and mixing solid raw materials, a device for conveying solid materials, an oxygen-enriched calcium carbide furnace, an oxygen-enriched air-blowing device, a tube-shell thermostatic reactor, a fixed bed tubular reactor, a fluidized bed reactor, an acetylene generator having a heat exchanger, a fixed bed reactor and a polymerization reactor; wherein:

a homogeneous mixture of limestone powder and carbon material powder is fed by the device for pulverizing and mixing solid raw materials and the device for conveying solid materials into the oxygen-enriched calcium carbide furnace;

one branch of product outlet of the oxygen-enriched calcium carbide furnace is sequentially connected with the acetylene generator having a heat exchanger and the fixed bed reactor, and the other branch is sequentially connected with the tube-shell thermostatic reactor, the fixed bed tubular reactor and the fluidized bed reactor to produce dichloroethane, and both of the two branches are combined at the fixed bed reactor, which is connected with the polymerization reactor;

the oxygen-enriched calcium carbide furnace is provided with a plasma ignition combustion-supporting device and a furnace temperature detection and control device; and the oxygen-enriched calcium carbide furnace is further provided with a solid material inlet and an oxygen-enriched gas inlet, wherein oxygen is input therein by the oxygen-enriched air-blowing device through the gas inlet; and shaft furnace of the oxygen-enriched calcium carbide furnace is provided with a first syngas outlet at the upper portion thereof, and a solid material outlet for exporting calcium carbide at the bottom portion thereof;

the acetylene generator having a heat exchanger is provided with a first material inlet, a second gas outlet and a first material outlet, and sequentially connected to a screw conveyer and a post-treatment device;

the fixed bed tubular reactor is provided with an ethanol inlet, an ethylene outlet, a first heat carrying medium inlet and a first heat carrying medium outlet;

the fluidized bed reactor is provided with an ethylene inlet, dichloroethane outlet, a second heat carrying medium inlet and a second heat carrying medium outlet; and the fixed bed reactor is provided with a second material inlet, a third material inlet and a second material outlet.

8. The loop-route production system for polyvinyl chloride according to claim 7, characterized in that, the polymerization reactor is subsequently connected with a separation and drying equipment, or with a screw extrusion device driven by a driving unit, or with a device for in-mold or out-of-mold laminated calculus mixing granulation driven by a driving unit.

9. The loop-route production system for polyvinyl chloride according to claim 7, characterized in that, a natural gas processing equipment is additionally provided adjacent to the acetylene generator having a heat exchanger, and interconnected with the acetylene generator having a heat exchanger through the first material inlet or directly.

10. The loop-route production system for polyvinyl chloride according to claim 7, characterized in that, a bioethanol processing device is additionally provided adjacent to the fixed bed tubular reactor, and interconnected with the material inlet of the fixed bed tubular reactor.

* * * * *